United States Patent [19]

Schacht et al.

[11] 4,069,338

[45] Jan. 17, 1978

[54] INDOLE DERIVATIVES AND PROCESS FOR THEIR PREPARATION

[75] Inventors: Erich Schacht; Werner Mehrhof; Detlev Kayser; Zdenek Simane, all of Darmstadt, Germany

[73] Assignee: Merck Patent Gesellschaft mit beschrankter Haftung, Darmstadt, Germany

[21] Appl. No.: 676,561

[22] Filed: Apr. 13, 1976

[30] Foreign Application Priority Data

Apr. 22, 1975 Germany .............................. 2517659

[51] Int. Cl.$^2$ .................. C07D 209/18; A61K 31/405
[52] U.S. Cl. ............................. 424/274; 260/326.13 R
[58] Field of Search .............. 260/326.13 R, 326.13 B; 424/274

[56] References Cited

U.S. PATENT DOCUMENTS 3,865,838  2/1975  Popelak et al. ............. 260/326.13 R Primary Examiner—Joseph Paul Brust
Assistant Examiner—Robert C. Whittenbaugh
Attorney, Agent, or Firm—Millen & White

[57] ABSTRACT

Indole derivatives of the formula

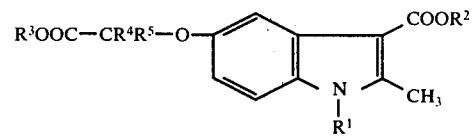

wherein $R^1$, $R^2$ and $R^3$ are identical or different and each is H or alkyl of 1 – 6 carbon atoms, $R^4$ is H or methyl and $R^5$ is methyl, phenyl or chlorophenyl, and their physiologically acceptable salts, are blood cholesterol-lowering agents.

15 Claims, No Drawings

INDOLE DERIVATIVES AND PROCESS FOR THEIR PREPARATION

BACKGROUND OF THE INVENTION

This invention relates to novel indole derivatives.

SUMMARY OF THE INVENTION

In a compositional aspect, this invention relates to novel indole compounds of Formula I

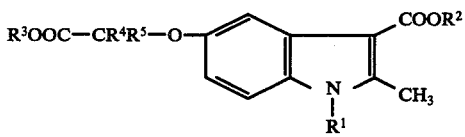

wherein $R^1$, $R^2$ and $R^3$ are identical or different and each is H or alkyl of 1–6 carbon atoms; $R^4$ is H or methyl and $R^5$ is methyl, phenyl or chlorophenyl, and physiologically acceptable salts thereof.

In another compositional aspect, this invention relates to a cholesterol-lowering pharmaceutical composition comprising a compound of Formula I, in admixture with a pharmaceutically-acceptable carrier.

In a method-of-use aspect, this invention relates to lowering the cholesterol level in the blood of mammals by administering to a patient a daily dosage of a compound of Formula I, in admixture with a pharmaceutically acceptable carrier, effective to lower the cholesterol level.

In another aspect, this invention relates to a process for preparing compounds of Formula I and their physiologically acceptable salts, wherein a. a 5-hydroxyindole of Formula II

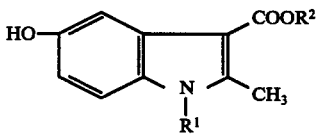

wherein $R^1$ and $R^2$ are as above, is reacted with a carboxylic acid compound of Formula III

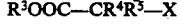

wherein X is Hal, OH or esterified OH and Hal is Cl, Br or I, and $R^3$, $R^4$ and $R^5$ are as above;

b. a compound of Formula IV

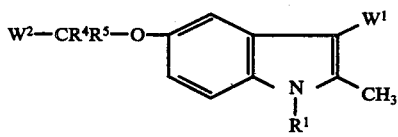

wherein $W^1$ and $W^2$ are functionally modified carboxyl groups, one of which can be free carboxyl, and $R^1$, $R^4$ and $R^5$ are as above, is treated with a solvolyzing agent; and, if desired, one or more of $R^1$, $R^2$, $R^3$ and/or $R^4$ in a compound of Formula I is converted into one or more different $R^1$, $R^2$, $R^3$ and/or $R^4$ by treatment with solvolyzing, esterifying, transesterifying and/or alkylating agents, and/or an acid of Formula I is converted to a physiologically acceptable salt by treatment with a base.

DETAILED DESCRIPTION

In compounds of Formula I, $R^1$, $R^2$, and $R^3$ are each H, methyl, ethyl, n-propyl, isopropyl, n-butyl, isobutyl, sec.-butyl, tert.-butyl, n-pentyl, 2- or 3-pentyl, 2-methyl-1-butyl, 3-methyl-1-butyl (isopentyl), 3-methyl-2-butyl, 2-methyl-2-butyl (tert.-pentyl), 2,2-dimethyl-1-propyl (neopentyl), n-hexyl, 2- or 3-hexyl, 2-methyl-1-pentyl, 2-methyl-2-pentyl, 2-methyl-3-pentyl, 3-methyl-1-pentyl, 3-methyl-2-pentyl, 3-methyl-3-pentyl, 4-methyl-1-pentyl (isohexyl), 4-methyl-2-pentyl, 2,3-dimethyl-1-butyl, 2,3-dimethyl-2-butyl, 2,2-dimethyl-1-butyl, 3,3-dimethyl-1-butyl or 3,3-dimethyl-2-butyl.

$R^1$ is preferably H or alkyl of 1–4 carbon atoms, most preferably, methyl, ethyl, n-propyl, isopropyl or isobutyl, but can be n-butyl, sec.-butyl, tert.-butyl, n-pentyl, isopentyl, neopentyl, n-hexyl or isohexyl. $R^2$ is preferably ethyl, H or methyl. $R^3$ is preferably H, ethyl, or methyl. $R^4$ is preferably methyl. $R^5$ can be o- or m-chlorophenyl, but preferably is methyl, phenyl or p-chlorophenyl.

Particularly preferred compounds of Formula I are those in which at least one of $R^1$ to $R^5$ is one of the preferred groups.

Preferred compounds of Formula I include the following wherein:

a. $R^1$ is H or alkyl of 1 – 4 carbon atoms;
b. $R^1$ is H, methyl, ethyl, n-propyl, isopropyl or isobutyl;
c. $R^2$ is H, methyl or ethyl, including (a) – (b) above;
d. $R^2$ is H, including (a) – (b) above;
e. $R^2$ is methyl or ethyl, including (a) – (b) above;
f. $R^3$ is H, methyl or ethyl; including (a) – (e) above;
g. $R^3$ is H, including (a) – (e) above;
h. $R^3$ is methyl or ethyl, including (a) – (e) above;
I. $R^1$ is H or alkyl of 1 – 4 carbon atoms and $R^2$ and $R^3$ each are H, methyl or ethyl;
j. $R^1$ is H, methyl, ethyl, n-propyl, isopropyl or isobutyl; $R^2$ and $R^3$ each are H or ethyl and $R^5$ is methyl, phenyl or p-chlorophenyl; and
k. $R^1$ is isopropyl or isobutyl, $R^2$ is ethyl, $R^3$ is H or ethyl and $R^5$ is methyl, phenyl or chlorophenyl.

X is preferably Cl or Br, but can be free OH, I or alkylsulfonyloxy of 1 – 6 carbon atoms, for example, methanesulfonyloxy; arylsulfonyloxy of 6 – 10 carbon atoms, for example, benzenesulfonyloxy, p-toluenesulfonyloxy or 1- or 2- naphthalenesulfonyloxy or alkanoyloxy of 1 – 7 carbon atoms, for example, acetoxy or benzyloxy.

Compounds of Formula I are prepared by known methods, as described in standard works including Houben-Weyl, Methoden der Organischen Chemie (Methods of Organic Chemistry), GeorgThieme-Varlag, Stuttgart, under conditions known to be suitable for these reactions. Known variants, not described in more detail here, can also be used.

Starting materials for preparing compounds of Formula I are known or can be prepared by known processes. 5-Hydroxyindoles of Formula II can be obtained by reacting p-benzoquinone with a 3-amino-2-butenoic acid ester of the formula $CH_3-C(NHR^1)=CH-COOA$, wherein A is alkyl of 1 – 6 carbon atoms, and, if desired, saponifying the resulting ester of Formula II ($R^2$ is A) in an alkaline medium. Most of the carboxylic acid derivatives of Formula III are known. They are obtainable by halogenation and, if desired, subsequent hydrolysis and esterification of carboxylic acid derivatives of the formula $R^3OOC—CHR^4R^5$. Indole derivatives of Formula IV can be prepared by reaction of corresponding hydroxyindoles, analogous to Formula II, but substituted by $W^1$ instead of $COOR^2$, with carboxylic acid derivatives of the formula $W^2—CR^4R^5-X$.

The above starting materials can be formed in situ, so that they are not isolated from the reaction mixture but reacted directly to give compounds of Formula I.

Preferably, compounds of Formula I are obtained by reaction of 5-hydroxyindoles of Formula II with carboxylic acid derivatives of Formula III. Hydroxyindole II can first be converted to a salt, particularly a metal salt, such as an alkali metal salt, preferably a Li, Na or K salt. To form the salt, the hydroxyindole is reacted with a reagent which forms metal salts, for example, an alkali metal such as Na; an alkali metal hydride or alkali metal amide such as LiH, NaH, $NaNH_2$ or $KNH_2$; a lower alkali metal alcoholate, such as lithium methylate, ethylate or tert.-butylate, sodium methylate, ethylate or tert.-butylate or potassium methylate, ethylate or tert.-butylate; an organometallic compound such as butyllithium, phenyllithium or phenylsodium; or a metal hydroxide, carbonate or bicarbonate, such as lithium hydroxide, carbonate or bicarbonate, sodium hydroxide, carbonate or bicarbonate, potassium hydroxide, carbonate or bicarbonate or calcium hydroxide, carbonate or bicarbonate. The salt is preferably prepared in a solvent, for example, a hydrocarbon such as hexane, benzene, toluene or xylene; an ether such as diethyl ether, diisopropyl ether, tetrahydrofuran (THF), dioxane or diethylene glycol dimethyl ether; an amide such as dimethylformamide (DMF) or phosphoric acid hexamethyltriamide (HMPT); an alcohol such as methanol or ethanol; a ketone such as acetone or butanone; or a solvent mixture. Hydroxyindole II or a salt thereof is reacted with a carboxylic acid derivative III, preferably in the presence of a diluent, e.g., the solvent used to prepare the salt, though this solvent can be replaced by or diluted with another solvent. The reaction is done at temperatures between -20° and 150°, preferably between 20° and 120°, most conveniently at the boiling point of the solvent. It can be carried out under an inert gas, for example, nitrogen. The salt can be formed in situ; in that case, hydroxyindole II and compound III are allowed to react with one another in the presence of the salt-forming reagent.

A particularly preferred method is to heat compounds II and III (X is Cl or Br and $R^1$ is $CH_3$ or $C_2H_5$) under reflux with an alcoholic, for example, ethanolic, sodium alcoholate solution for 2 to 8 hours.

Free hydroxyindole II can be reacted with a hydroxyacid derivative of Formula III (X is OH), preferably in the presence of a condensing agent. Suitable condensing agents include acidic dehydration catalysts, for example, mineral acids such as sulfuric acid or phosphoric acid, as well as P-toluenesulfonyl chloride, arsenic acid, boric acid, $NaHSO_4$ or $KHSO_4$, diaryl carbonates, for example, diphenyl carbonate, dialkyl carbonates, for example, dimethyl carbonate or diethyl carbonate, or carbodiimides, for example, dicyclohexylcarbodiimide. If an acid is used as condensing agent, the reaction is suitably carried out in an excess of acid at temperatures between about 0° and about 100° C., preferably between 50° and 60° C. Diluents, including benzene, toluene or dioxane, can be added. A carbonic acid ester is preferably used at a higher temperature, from about 100° to about 210° C., most preferably between 180°and 200° C. A transesterification catalyst such as sodium carbonate, potassium carbonate or sodium methylate can be added.

Indole derivatives of Formula I are also obtained by solvolysis, preferably hydrolysis, of other indole derivatives of Formula IV. In these, $W^1$ can be $COOR^2$. If $W^1$ is not $COOR^2$, $W^2$ can be $COOR^3$. Otherwise, $W^1$ and/or $W^2$ are one of the following, wherein R' and R" which are to be split off can be radicals of any kind and can each be alkyl of preferably 1 – 4 carbon atoms, can be identical or different, and can collectively be tetramethylene or pentamethylene, optionally interrupted by O; $C(Hal)_3$; COOR''', wherein R''' is different from $R^2$ and $R^3$, particularly alkyl of 5 – 12 carbon atoms or a substituted alkyl different from $R^2$ and $R^3$; $C(OR')_3$; COOAcyl, wherein Acyl is derived from a carboxylic acid of up to 24 carbon atoms; CN; $COHN_2$; CONHR'; CONR'R"; CONHOH; C(OH)=NOH; $CONHNH_2$; $CON_3$; $C(OR')=NH$; $C(NH_2)=NNH_2$; $C(NHNH_2)=NH$; CSOH; COSH; CSOR'; $CSNH_2$; CSNHR'; or CSNR'R". Preferably, at least one $W^1$ and $W^2$ is a nitrile or amide.

Hydrolysis of compounds of Formula IV can be carried out in acid or alkaline media at temperatures between about -20°and 300°, preferably at the boiling point of the solvent chosen. Suitable acid catalysts include hydrochloric acid, sulfuric acid, phosphoric acid or hydrobromic acid; preferred basic catalysts are sodium hydroxide, potassium hydroxide or calcium hydroxide, sodium carbonate or potassium carbonate. Preferred solvents include water, lower alcohols such as methanol or ethanol, ethers such as THF or dioxane, amides such as DMF, nitriles such as acetonitrile, sulfones such as tetramethylenesulfone, or mixtures thereof, particularly mixtures containing water.

Hydrolysis of nitriles (IV, $W^1$ and/or $W^2$ is CN) or amides (IV, $W^1$ and/or $W^2$ is $CONH_2$, CONHR' or CONR'R") is conveniently carried out in an acid medium, for example, with acetic acid/hydrochloric acid, or an alkaline medium, for example, with alcoholic alkali.

Esters of Formula I ($R^2$ and/or $R^3$ is A) can also be prepared by solvolysis. For example, nitriles IV ($W^1$ and/or $W^2$ is CN) can be converted to the corresponding iminoalkylether hydrochlorides by reaction with alcoholic hydrochloric acid, and these can be converted to the corresponding alkyl esters by partial hydrolysis.

If desired, one or more of $R^1$, $R^2$, $R^3$ and/or $R^4$ in a compound of Formula I can be converted by solvolysis, esterification, transesterification and/or alkylation, to one or more different $R^1$, $R^2$, $R^3$ and/or $R^4$.

For example, in a compound of Formula I, $R^2$ and/or $R^3$ can be converted to another $R^2$ and/or $R^3$ by treatment with solvolyzing agents. More particularly, an ester of Formula I ($R^2$ and/or $R^3$ is A) can be saponified to the corresponding acid I ($R^2$ and/or $R^3$ is H). The solvolysis or saponification can be done by one of the methods indicated above for solvolysis of compounds of Formula IV. Preferably, the esters are saponified by treatment with alcoholic alkali solutions, for example, ethanolic potassium hydroxide, at temperatures between about 20° and 120° C., preferably under reflux. If both $R^2$ and $R^3$ (identical or different groups) are A, $COOR^3$ is saponified first under these conditions so that monoesters of Formula I ($R^2$ is A and $R^3$ is H) are easily obtained by partial saponification of diesters of Formula I ($R^2$ and $R^3$ are A). Saponification of these diesters or monoesters under more drastic conditions, for example, longer reaction times, gives dicarboxylic acids of Formula I ($R^2$ and $R^3$ are H).

An acid of Formula I ($R^2$ and/or $R^3$ is H) can be esterified with an alcohol of formula A-OH, preferably in the presence of an inorganic or organic acid, e.g., HCl, HBr, HI, $H_2SO_4$, $H_3PO_4$, trifluoroacetic acid, benzenesulfonic acid or p-toluenesulfonic acid; or an acid ion exchange resin, if appropriate, in the presence of an inert solvent, such as benzene, toluene or xylene, at temperatures between 0°, preferably at the boiling point. The alcohol is preferably employed in excess. Esters can also be obtained by reaction of carboxylic acids with diazoalkanes, for example, diazomethane. Esters can also be prepared by reaction of metal salts of acids I ($R^2$ and/or $R^3$ is H), preferably alkali metal salts, lead salts or silver salts, with halides of the formula A-Hal. The esterification can also be carried out in several steps. It is possible first to prepare the corresponding acid halide, for example, an acid chloride, from acid I ($R^2$ and/or $R^3$ is H) and to react this halide with an alcohol A-OH, if appropriate, in the presence of an acid or basic catalyst.

Esters of Formula I ($R^2$ and/or $R^3$ is A) can be obtained by transesterification, particularly by reaction of other esters with an excess of a particular alcohol or by reaction of carboxylic acids I ($R^2$ and/or $R^3$ is H) with other esters of the particular alcohol, preferably alkanoates wherein the alkanoyl radical has up to 4 carbon atoms, particularly in the presence of basic or acid catalysts, for example, sodium ethylate or sulfuric acid, at temperatures between 0° and, preferably, the boiling point.

A compound of Formula I ($R^1$ and/or $R^4$ is H) can be alkylated to a compound of Formula I ($R^1$ is A and/or $R^4$ is methyl).

Examples of alkylating agents include methyl chloride, bromide, iodide and p-toluenesulfonate and dimethyl sulfate. When $R^1$ is H, ethyl chloride, bromide or iodide, n-propyl chloride, bromide or iodide, n-propyl chloride, bromide or iodide, isopropyl chloride, bromide or iodide and isobutyl chloride, bromide or iodide can be used. Compounds of Formula I are preferably converted to their metal derivatives prior to alkylation, by reaction with an alcoholate such as sodium ethylate or potassium tert.-butylate, a hydride such as sodium hydride, an amide such as sodium amide or lithium diisopropylamide, an organometallic compound such as n-butyl Li or a metal such as sodium in liquid ammonia. This conversion is generally carried out in an inert solvent, for example, an alcohol such as methanol, ethanol or tert.-butanol; an ether such as diethyl ether; an amide such as DMF or HMPT or a hydrocarbon such as benzene, or in mixtures thereof. The alkylation is preferably carried out subsequently in the same reaction mixture. Reaction temperatures are between about −20° and +120° C., preferably between 0° and 80° C., and reaction times are preferably between about 1 and 48 hours.

An acid of Formula I ($R^2$ and/or $R^3$ is H) can be converted to a physiologically acceptable metal or ammonium salt by reaction with a base. Salts which can be prepared include sodium, potassium, magnesium, calcium and ammonium salts, as well as substituted ammonium salts, for example, dimethylammonium, diethylammonium, diisopropylammonium, monoethanolammonium, diethanolammonium, triethanolammonium, cyclohexylammonium, dicyclohexylammonium and dibenzylethylenediammonium salts.

Compounds of Formula I can be liberated from their metal and ammonium salts by treatment with acids.

Compounds of Formula I can contain one or more centers of asymmetry and are usually in the racemic form. The racemates can be separated into their optical antipodes by methods given in the literature. It is possible to obtain optically active compounds by the methods described from optically active starting materials.

Compounds of Formula I and salts thereof are well tolerated and have outstanding properties of lowering the cholesterol, triglyceride, and uric acid levels of the blood and inducing liver enzyme activity. Lowering of cholesterol level in the serum of rats can be measured by the method of Levine et al. (Automation in Analytical Chemistry, Technicon Symposium 1967, Mediad, New York, pages 25–28). Lowering of the triglyceride level can be measured by the method of Noble and Campbell (Clin. Chem. 16 (1970), pages 166–170).

Compounds of Formula I and physiologically acceptable salts thereof can be used as medicaments and as intermediates for the preparation of other medicaments, including the corresponding amides.

Compounds of Formula I and/or their physiologically acceptable salts can be used, mixed with solid, liquid and/or semi-liquid medicinal excipients, as medicaments in human medicine or veterinary medicine. Excipients are organic or inorganic material which are suitable for enteral, parenteral or topical administration and which do not react with the new compounds, for example, water, vegetable oils, benzyl alcohols, polyethylene glycols, gelatins, lactose, starch, magnesium stearate, talc and petroleum jelly. For enteral administration it is possible to use, for example, tablets, dragees, capsules, syrups, elixirs or suppositories. For enteral administration, solutions, preferably oily or aqueous solutions, are preferred. Suspensions, emulsions or implants can be used. Ointments, creams or powders are for topical application. The new compounds can by lyophilized and the resulting lyophilizates can be used to prepare injectable formulations. Any of the foregoing formulations can be sterilized and/or contain auxiliaries, including lubricants, preservatives, stabilizers and/or wetting agents, emulsifiers, osmotic pressure regulators, buffers, colorants, flavoring agents and/or aromatic agents. The can also contain one or more additional active compounds, for example, vitamins.

The new indole compounds are administered in the manner of the known compound clofibrat, preferably in dosages of between about 10 and 1,000 mg., and especially between 50 and 500 mg. per dosage unit. The daily dosage is preferably between 0.2 and 20 mg./kg. of body weight. Oral administration is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

Each of the compounds of Formula I given in the examples which follow is particularly suitable for the preparation of pharmaceutical formulations.

EXAMPLE 1 a. 27.5 g. of 1-isobutyl-2-methyl-3-carbethoxy-5-hydroxyindole, obtainable from 1,4-benzoquinone and 3-isobutylaminocrotonic acid ethyl ester, and 39 g. of 2-bromo-2-methylpropionic acid ethyl ester, are added to a solution of 4.6 g. of sodium in 300 ml. of ethanol. The mixture is stirred and heated under reflux for 18 hours. After evaporation of solvent, water is added to the residue and the mixture is extracted with chloroform. 2-(1-Isobutyl-2-methyl-3-carbethoxyindolyl-5-oxy)-2-methylpropionic acid ethyl ester (hereafter, "ester Ih"), b.p. 195°/0.05 mm., is obtained.

By the same method, 5-hydroxyindole derivatives and 2-bromopropionic acid ethyl ester, 2-bromo-2-methylpropionic acid ethyl ester, 2-bromo-2-phenylacetic acid ethyl ester, 2-bromo-2-o-chlorophenyl-, 2-bromo-2-m-chlorophenyl- or 2-bromo-2-p-chlorophenylacetic acid ethyl ester or -propionic acid ethyl ester given the following:

2-(2-methyl-3-carbethoxyindolyl-5-oxy)-propionic acid ethyl ester;
2-(1,2-dimethyl-3-carbethoxyindolyl-5-oxy)-propionic acid ethyl ester;
2-(1-ethyl-2-methyl-3-carbethoxyindolyl-5-oxy)-propionic acid ethyl ester;
2-(1-n-propyl-2-methyl-3-carbethoxyindolyl-5-oxy)-propionic acid ethyl ester;
2-(1-isopropyl-2-methyl-3-carbethoxyindolyl-5-oxy)-propionic acid ethyl ester;
2-(1-isobutyl-2-methyl-3-carbethoxyindolyl-5-oxy)-propionic acid ethyl ester;
2-(2-methyl-3-carbethoxyindolyl-5-oxy)-2-methylpropionic acid ethyl ester;
2-(1,2-dimethyl-3-carbethoxyindolyl-5-oxy)-2-methylpropionic acid ethyl ester;
2-(1-ethyl-2-methyl-3-carbethoxyindolyl-5-oxy)-2-methylpropionic acid ethyl ester;
2-(1-n-propyl-2-methyl-3-carbethoxyindolyl-5-oxy)-2-methylpropionic acid ethyl ester;
2-(1isopropyl-2-methyl-3-carbethoxyindolyl-5-oxy)-2-methylpropionic acid ethyl ester, $n_D^{20}$ 1.5368;
2-(1-n-butyl-2-methyl-3-carbethoxyindolyl-5-oxy)-2-methylpropionic acid ester;
2-(1-sec.-butyl-2-methyl-3-carbethoxyindolyl-5-oxy)-2-methylpropionic acid ethyl ester;
2-(1-tert.-butyl-2-methyl-3-carbethoxyindolyl-5-oxy)-2-methylpropionic acid ethyl ester;
2-(1-n-pentyl-2-methyl-3-carbethoxyindolyl-5-oxy)-2-methylpropionic acid ethyl ester;
2-(1-isopentyl-2-methyl-3-carbethoxyindolyl-5-oxy)-2-methylpropionic acid ethyl ester;
2-(1-neopentyl-2-methyl-3-carbethoxyindolyl-5-oxy)-2-methylpropionic acid ethyl ester;
2-(1-n-hexyl-2-methyl-3-carbethoxyindolyl-5-oxy)-2-methylpropionic aicd ethyl ester;
2-isohexyl-2-methyl-3carbethoxyindolyl-5-oxy)-2-methylpropionic acid ethyl ester,
2-(2-methyl-3-carbethoxyindolyl-5-oxy)-2-phenylacetic acid ethyl ester;
2-(1,2-dimethyl-3-carbethoxyindolyl-5-oxy)-2phenylacetic acid ethyl ester;
2-(1-methyl-3-carbethoxyindolyl-5-oxy)-2-phenylacetic acid ethyl ester;
2-(1-n-propyl-2-methyl-3-carbethoxyindolyl-5-oxy)-2-phenylacetic acid ethyl ester;
2-(1-isopropyl-2-methyl-3-carbethoxyindolyl-5-oxy)-2-phenylacetic acid ethyl ester;
2-(1-isobutyl-2-methyl-3-carbethoxyindolyl-5-oxy)-2-phenylacetic acid ethyl ester,
2-(2-methyl-3-carbethoxyindolyl-5-oxy)-2-phenylpropionic acid ethyl ester;
2(1,2-dimethyl-3-carbethoxyindolyl-5-oxy)-2-phenylpropionic acid ethyl ester;
2-(1-ethyl-2-methyl-3-carbethoxyindolyl-5-oxy)-2-phenylpropionic acid ethyl ester;
2-(1-n-propyl-2-methyl-3-carbethoxyindolyl-5-oxy)-2-phenylpropionic acid ethyl ester;
2-(1-isopropyl-2methyl-3-carbethoxyindolyl-5-oxy)-2-phenylpropionic acid ethyl ester;
2-(1-isobutyl-2-methyl-3-carbethoxyindolyl-5-oxy)-2-phenylpropionic acid ethyl ester;
2-(2-methyl-3-carbethoxyindolyl-5-oxy)-2-o-chlorophenylacetic acid ethyl ester;
2-(1,2-dimethyl-3-carbethoxyindolyl-5-oxy)-2-o-chlorophenylacetic acid ethyl ester;
2-(1-ethyl-2-methyl-3-carbethoxyindolyl-5-oxy)-2-o-chlorophenylacetic acid ethyl ester;
2-(1-n-propyl-2methyl-3-carbethoxyindolyl-5-oxy)-2-o-chlorophenylacetic acid ethyl ester;
2-(1-isopropyl-2-methyl-3-carbethoxyindolyl-5-oxy)-2-o-chlorophenylacetic acid ethyl ester;
2-(1-isobutyl-2-methyl-3-carbethoxyindolyl-5-oxy)-2-o-chlorophenylacetic acid ethyl ester;
2-(2-methyl-3-carbethoxyindolyl-5-oxy)-2-o-chlorophenylpropionic acid ethyl ester;
2-(1,2-dimethyl-3-carbethoxyindolyl-5-oxy)-2-o-chlorophenylpropionic acid ethyl ester;
2-(1-ethyl-2-methyl-3-carbethoxyindolyl-5-oxy)-2-o-chlorophenylpropionic acid ethyl ester;
2-(1-n-propyl-2-methyl-3-carbethoxyindolyl-5-oxy)-2-o-chlorophenylpropionic acid ethyl ester;
2-(1-isopropyl-2-methyl-3-carbethoxyindolyl-5-oxy)-2-o-chlorophenylpropionic acid ethyl ester;
2-(1-isobutyl-2-methyl-3-carbethoxyindolyl-5-oxy)-2-o-chlorophenylpropionic acid ethyl ester;
2-(2-methyl-3-carbethoxyindolyl-5-oxy)-2-m-chlorophenylacetic acid ethyl ester;
2-(1,2-dimethyl-3-carbethoxyindolyl-5-oxy)-2-m-chlorophenylacetic acid ethyl ester;
2-(1-ethyl-2-methyl-3-carbethoxyindolyl-5oxy)-2-m-chlorophenylacetic acid ethyl ester;
2-(1-n-propyl-2-methyl-3-carbethoxyindolyl-5-oxy)-2-m-chorophenylacetic acid ethyl ester;
2-(1-isopropyl-2-methyl-3-carbethoxyindolyl-5-oxy)-2-m-chlorophenylacetic acid ethyl ester;
2-isobutyl-2-methyl-3-carbethoxyindolyl-5-oxy)-2-m-chlorophenylacetic acid ethyl ester;
2-(2methyl-3-carbethoxyindolyl-5-oxy)-2-m-chlorophenylpropionic acid ethyl ester;
2-(1,2-dimethyl-3-carbethoxyindolyl-5-oxy)-2-m-chlorophenylpropionic acid ethyl ester;
2(1-ethyl-2-methyl-3-carbethoxyindolyl-5-oxy)-2-m-chlorophenylpropionic acid ethyl ester;
2-(1-n-propyl-2-methyl-3-carbethoxyindolyl-5-oxy)-2-m-chlorophenylpropionic acid ethyl ester;
2-(1-isopropyl-2-methyl-3-carbethoxyindolyl-5-oxy)-2-m-chlorophenylpropionic acid ethyl ester;
2-(1-isobutyl-2-methyl-3-carbethoxyindolyl-5-oxy)-2-m-chlorophenylpropionic acid ethyl ester;
2-(2-methyl-3-carbethoxyindolyl-5-oxy)-2-p-chlorophenylacetic acid ethyl ester;
2-(1,2-dimethyl-3-carbethoxyindolyl-5-oxy)-2-p-chlorophenylacetic acid ethyl ester;
2-(1-ethyl-2-methyl-3-carbethoxyindolyl-5oxy)-2-p-chlorophenylacetic acid ethyl ester;
2-(1-n-propyl-2-methyl-3-carbethoxyindolyl-5-oxy)-2-p-chlorophenylacetic acid ethyl ester;
2-(1-isopropyl-2-methyl-3-carbethoxyindolyl-5-oxy)-2-p-chlorophenylacetic acid ethyl ester;
2-(1-isobutyl-2-methyl-3-carbethoxyindolyl-5-oxy)-2-p-chlorophenylacetic acid ethyl ester;

2-(2-methyl-3-carbethoxyindolyl-5-oxy)-2-p-chlorophenylpropionic acid ethyl ester;
2-(1,2-dimethyl-3-carbethoxyindolyl-5-oxy)-2-p-chlorophenylpropionic acid ethyl ester;
2-(1-ethyl-2-methyl-3-carbethoxyindolyl-5-oxy)-2-p-chlorophenylpropionic acid ethyl ester;
2-(1-n-propyl-2-methyl-3-carbethoxyindolyl-5-oxy)-2-p-chlorophenylpropionic acid ethyl ester;
2-(1-isopropyl-2-methyl-3-carbethoxyindolyl-5-oxy)-2-p-chlorophenylpropionic acid ethyl ester, and
2-(1-isobutyl-2-methyl-3-carbethoxyindolyl-5-oxy)-2-p-chlorophenylpropionic acid ethyl ester.

b. 8 g. of ester Ih are heated under reflux with 2.4 g. of KOH in 80 ml. of ethanol for 2 hours and the mixture is evaporated. Water is added to the residue, and the solution is washed with ether and brought to pH 5 with hydrochloric acid. 2-(1-Isobutyl-2-methyl-3-carbethoxyindolyl-5-oxy)-2-methylpropionic acid (hereafter, "acid Ii") is filtered off. m.p. 123°–125°.

The following are obtained in a similar fashion by saponification of the corresponding ethyl esters:

2-(2-methyl-3-carbethoxyindolyl-5-oxy)-propionic acid;
2-(1,2-dimethyl-3-carbethoxyindolyl-5-oxy)-propionic acid;
2-(1-ethyl-2-methyl-3-carbethoxyindolyl-5-oxy)-propionic acid;
2-(1-n-propyl-2-methyl-3-carbethoxyindolyl-5-oxy)-propionic acid;
2-(1-isopropyl-2-methyl-3-carbethoxyindolyl-5-oxy)-propionic acid;
2-(1-isobutyl-2-methyl-3-carbethoxyindolyl-5-oxy)-propionic acid;
2-(2-methyl-3-carbethoxyindolyl-5-oxy)-2-methylpropionic acid;
2-(1,2-dimethyl-3-carbethoxyindolyl-5-oxy)-2-methylpropionic acid;
2-(1-ethyl-2-methyl-3-carbethoxyindolyl-5-oxy)-2-methylpropionic acid;
2-(1-n-propyl-2-methyl-3-carbethoxyindolyl-5-oxy)-2-methylpropionic acid;
2-(1-isopropyl-2-methyl-3-carbethoxyindolyl-5-oxy)-2-methylpropionic acid, m.p. 125°;
2-(1-n-butyl-2-methyl-3-carbethoxyindolyl-5-oxy)-2-methylpropionic acid;
2-(1-sec.-butyl-2-methyl-3-carbethoxyindolyl-5-oxy)-2-methylpropionic acid;
2-(1-tert.-butyl-2-methyl-3-carbethoxyindolyl-5-oxy)-2-methylpropionic acid;
2-(1-n-pentyl-2-methyl-3-carbethoxyindolyl-5-oxy)-2-methylpropionic acid;
2-(1-isopentyl-2-methyl-3-carbethoxyindolyl-5-oxy)-2-methylpropionic acid;
2-(1-neopentyl-2-methyl-3-carbethoxyindolyl-5-oxy)-2-methylpropionic acid;
2-(1-n-hexyl-2-methyl-3-carbethoxyindolyl-5-oxy)-2-methylpropionic acid;
2-(1-isohexyl-2-methyl-3-carbethoxyindolyl-5-oxy)-2-methylpropionic acid;
2-(2-methyl-3-carbethoxyindolyl-5-oxy)-2-phenylacetic acid;
2-(1,2-dimethyl-3-carbethoxyindolyl-5-oxy)-2-phenylacetic acid;
2-(1-ethyl-2-methyl-3-carbethoxyindolyl-5-oxy)-2-phenylacetic acid;
2-(1-n-propyl-2-methyl-3-carbethoxyindolyl-5-oxy)-2-phenylacetic acid;
2-(1-isopropyl-2-methyl-3-carbethoxyindolyl-5-oxy)-2-phenylacetic acid;
2-(1-isobutyl-2-methyl-3-carbethoxyindolyl-5-oxy)-2-phenylacetic acid;
2-(2-methyl-3-carbethoxyindolyl-5-oxy)-2-phenylpropionic acid;
2-(1,2-dimethyl-3-carbethoxyindolyl-5-oxy)-2-phenylpropionic acid;
2-(1-ethyl-2-methyl-3-carbethoxyindolyl-5-oxy)-2-phenylpropionic acid;
2-(1-n-propyl-2-methyl-3-carbethoxyindolyl-5-oxy)-2-phenylpropionic acid;
2-(1-isopropyl-2-methyl-3-carbethoxyindolyl-5-oxy)-2-phenylpropionic acid;
2-(1-isobutyl-2-methyl-3-carbethoxyindolyl-5-oxy)-2-phenylpropionic acid, m.p. 146°–148°, cyclohexylamine salt, m.p. 182°–184°;
2-(2-methyl-3-carbethoxyindolyl-5-oxy)-2-o-chlorophenylacetic acid;
2-(1,2-dimethyl-3-carbethoxyindolyl-5-oxy)-2-o-chlorophenylacetic acid;
2-(1-ethyl-2-methyl-3-carbethoxyindolyl-5-oxy)-2-o-chlorophenylacetic acid;
2-(1-n-propyl-2-methyl-3-carbethoxyindolyl-5-oxy)-2-o-chlorophenylacetic acid;
2-(1-isopropyl-2-methyl-3-carbethoxyindolyl-5-oxy)-2-o-chlorophenylacetic acid;
2-(1-isobutyl-2-methyl-3-carbethoxyindolyl-5-oxy)-2-o-chlorophenylacetic acid;
2-(2-methyl-3-carbethoxyindolyl-5-oxy)-2-o-chlorophenylpropionic acid;
2-(1,2-dimethyl-3-carbethoxyindolyl-5-oxy)-2-o-chlorophenylpropionic acid;
2-(1-ethyl-2-methyl-3-carbethoxyindolyl-5-oxy)-2-o-chlorophenylpropionic acid;
2-(1-n-propyl-2-methyl-3-carbethoxyindolyl-5-oxy)-2-o-chlorophenylpropionic acid;
2-(1-isopropyl-2-methyl-3-carbethoxyindolyl-5-oxy)-2-o-chlorophenylpropionic acid;
2-(1-isobutyl-2-methyl-3-carbethoxyindolyl-5-oxy)-2-o-chlorophenylpropionic acid;
2-(2-methyl-3-carbethoxyindolyl-5-oxy)-2-m-chlorophenylacetic acid;
2-(1,2-dimethyl-3-carbethoxyindolyl-5-oxy)-2-m-chlorophenylacetic acid;
2-(1-ethyl-2-methyl-3-carbethoxyindolyl-5-oxy)-2-m-chlorophenylacetic acid;
2-(1-n-propyl-2-methyl-3-carbethoxyindolyl-5-oxy)-2-m-chlorophenylacetic acid;
2-(1-isopropyl-2-methyl-3-carbethoxyindolyl-5-oxy)-2-m-chlorophenylacetic acid;
2-(1-isobutyl-2-methyl-3-carbethoxyindolyl-5-oxy)-2-m-chlorophenylacetic acid;
2-(2-methyl-3-carbethoxyindolyl-5-oxy)-2-m-chlorophenylpropionic acid;
2-(1,2-dimethyl-3-carbethoxyindolyl-5-oxy)-2-m-chlorophenylpropionic acid;
2-(1-ethyl-2-methyl-3-carbethoxyindolyl-5-oxy)-2-m-chlorophenylpropionic acid;
2-(1-n-propyl-2-methyl-3-carbethoxyindolyl-5-oxy)-2-m-chlorophenylpropionic acid;
2-(1-isopropyl-2-methyl-3-carbethoxyindolyl-5-oxy)-2-m-chlorophenylpropionic acid;
2-(1-isobutyl-2-methyl-3-carbethoxyindolyl-5-oxy)-2-m-chlorophenylpropionic acid;
2-(2-methyl-3-carbethoxyindolyl-5-oxy)-2-p-chlorophenylacetic acid;

2-(1,2-dimethyl-3-carbethoxyindolyl-5-oxy)-2-p-chlorophenylacetic acid;
2-(1-ethyl-2-methyl-3-carbethoxyindolyl-5-oxy)-2-p-chlorophenylacetic acid;
2-(1-n-propyl-2-methyl-3-carbethoxyindolyl-5-oxy)-2-p-chlorophenylacetic acid;
2-(1-isopropyl-2-methyl-3-carbethoxyindolyl-5-oxy)-2-p-chlorophenylacetic acid;
2-(1-isobutyl-2-methyl-3-carbethoxyindolyl-5-oxy)-2-p-chlorophenylacetic acid;
2-(2-methyl-3-carbethoxyindolyl-5-oxy)-2-p-chlorophenylpropionic acid;
2-(1,2-dimethyl-3-carbethoxyindolyl-5-oxy)-2-p-chlorophenylpropionic acid;
2-(1-ethyl-2-methyl-3-carbethoxyindolyl-5-oxy)-2-p-chlorophenylpropionic acid;
2-(1-n-propyl-2-methyl-3-carbethoxyindolyl-5-oxy)-2-p-chlorophenylpropionic acid;
2-(1-isopropyl-2-methyl-3-carbethoxyindolyl-5-oxy)-2-p-chlorophenylpropionic acid, and
2-(1-isobutyl-2-methyl-3-carbethoxyindolyl-5-oxy)-2-p-chlorophenylpropionic acid.

c. 1 g. of acid Ii (or ester Ih) is heated under reflux with 0.5 g. of KOH in 15 ml. of isopropanol overnight (14 hours). The mixture is evaporated and water is added to the residue. The solution is washed with ether and treated with excess hydrochloric acid. 2-(1-Isobutyl-2-methyl-3-carboxyindolyl-5-oxy)-2-methylpropionic acid is obtained.

Saponification of corresponding diethyl esters or monoethyl esters listed under (a) and (b) above give the following:

2-(2-methyl-3-carboxyindolyl-5-oxy)-propionic acid;
2-(1,2-dimethyl-3-carboxyindolyl-5-oxy)-propionic acid;
2-(1-ethyl-2-methyl-3-carboxyindolyl-5-oxy)-propionic acid;
2-(1-n-propyl-2-methyl-3-carboxyindolyl-5-oxy)-propionic acid;
2-(1-isopropyl-2-methyl-3-carboxyindolyl-5-oxy)-propionic acid;
2-(1-isobutyl-2-methyl-3-carboxyindolyl-5-oxy)-propionic acid;
2-(2-methyl-3-carboxyindolyl-5-oxy)-2-methylpropionic acid;
2-(1,2-dimethyl-3-carboxyindolyl-5-oxy)-2-methylpropionic acid;
2-(1-ethyl-2-methyl-3-carboxyindolyl-5-oxy)-2-methylpropionic acid;
2-(1-n-propyl-2-methyl-3-carboxyindolyl-5-oxy)-2-methylpropionic acid;
2-(1-isopropyl-2-methyl-3-carboxyindolyl-5-oxy)-2-methylpropionic acid;
2-(1-n-butyl-2-methyl-3-carboxyindolyl-5-oxy)-2-methylpropionic acid;
2-(1-sec.-butyl-2-methyl-3-carboxyindolyl-5-oxy)-2-methylpropionic acid;
2-(1-tert.-butyl-2-methyl-3-carboyxindolyl-5-oxy)-2-methylpropionic acid;
2-(1-n-pentyl-2-methyl-3-carboxyindolyl-5-oxy)-2-methylpropionic acid;
2-(1-isopentyl-2-methyl-3-carboxyindolyl-5-oxy)-2-methylpropionic acid;
2-(1-neopentyl-2-methyl-3-carboxyindolyl-5-oxy)-2-methylpropionic acid;
2-(1-n-hexyl-2-methyl-3-carboxyindolyl-5-oxy)-2-methylpropionic acid;
2-(1-isohexyl-2-methyl-3-carboxyindolyl-5-oxy)-2-methylpropionic acid;
2-(2-methyl-3-carboxyindolyl-5-oxy)-2-phenylacetic acid;
2-(1,2-dimethyl-3-carboxyindolyl-5-oxy)-2-phenylacetic acid;
2-(1-ethyl-2-methyl-3-carboxyindolyl-5-oxy)-2-phenylacetic acid;
2-(1-n-propyl-2-methyl-3-carboxyindolyl-5-oxy)-2-phenylacetic acid;
2-(1-isopropyl-2-methyl-3-carboxyindolyl-5-oxy)-2-phenylacetic acid;
2-(1-isobutyl-2-methyl-3-carboxyindolyl-5-oxy)-2-phenylacetic acid;
2-(2-methyl-3-carboxyindolyl-5-oxy)-2-phenylpropionic acid;
2-(1,2-dimethyl-3-carboxyindolyl-5-oxy)-2-phenylpropionic acid;
2-(1-ethyl-2-methyl-3-carboxyindolyl-5-oxy)-2-phenylpropionic acid;
2-(1-n-propyl-2-methyl-3-carboxyindolyl-5-oxy)-2-phenylpropionic acid;
2-(1-isopropyl-2-methyl-3-carboxyindolyl-5-oxy)-2-phenylpropionic acid;
2-(1-isobutyl-2-methyl-3-carboxyindolyl-5-oxy)-2-phenylpropionic acid;
2-(2-methyl-3-carboxyindolyl-5-oxy)-2-o-chlorophenylacetic acid;
2-(1,2-dimethyl-3-carboxyindolyl-5-oxy)-2-o-chlorophenylacetic acid;
2-(1-ethyl-2-methyl-3-carboxyindolyl-5-oxy)-2-o-chlorophenylacetic acid;
2-(1-n-propyl-2-methyl-3-carboxyindolyl-5-oxy)-2-o-chlorophenylacetic acid;
2-(1-isopropyl-2-methyl-3-carboxyindolyl-5-oxy)-2-o-chlorophenylacetic acid;
2-(1-isobutyl-2-methyl-3-carboxyindolyl-5-oxy)-2-o-chlorophenylacetic acid;
2-(2-methyl-3-carboxyindolyl-5-oxy)-2-o-chlorophenylpropionic acid;
2-(1,2-dimethyl-3-carboxyindolyl-5-oxy)-2-o-chlorophenylpropionic acid;
2-(1-ethyl-2-methyl-3-carboxyindolyl-5-oxy)-2-o-chlorophenylpropionic acid;
2-(1-n-propyl-2-methyl-3-carboxyindolyl-5-oxy)-2-o-chlorophenylpropionic acid;
2-(1-isopropyl-2-methyl-3-carboxyindolyl-5-oxy)-2-o-chlorophenylpropionic acid;
2-(1-isobutyl-2-methyl-3-carboxyindolyl-5-oxy)-2-o-chlorophenylpropionic acid;
2-(2-methyl-3-carboxyindolyl-5-oxy)-2-m-chlorophenylacetic acid;
2-(1,2-dimethyl-3-carboxyindolyl-5-oxy)-2-m-chlorophenylacetic acid;
2-(1-ethyl-2-methyl-3-carboxyindolyl-5-oxy)-2-m-chlorophenylacetic acid;
2-(1-n-propyl-2-methyl-3-carboxyindolyl-5-oxy)-2-m-chlorophenylacetic acid;
2-(1-isopropyl-2-methyl-3-carboxyindolyl-5-oxy)-2-m-chlorophenylacetic acid;
2-(1-isobutyl-2-methyl-3-carboxyindolyl-5-oxy)-2-m-chlorophenylacetic acid;
2-(2-methyl-3-carboxyindolyl-5-oxy)-2-m-chlorophenylpropionic acid;
2-(1,2-dimethyl-3-carboxyindolyl-5-oxy)-2-m-chlorophenylpropionic acid;
2-(1-ethyl-2-methyl-3-carboxyindolyl-5-oxy)-2-m-chlorophenylpropionic acid;

2-(1-n-propyl-2-methyl-3-carboxyindolyl-5-oxy)-2-m-chlorophenylpropionic acid;
2-(1-isopropyl-2-methyl-3-carboxyindolyl-5-oxy)-2-m-chlorophenylpropionic acid;
2-(1-isobutyl-2-methyl-3-carboxyindolyl-5-oxy)-2-m-chlorophenylpropionic acid;
2-(2-methyl-3-carboxyindolyl-5-oxy)-2-p-chlorophenylacetic acid;
2-(1,2-dimethyl-3-carboxyindolyl-5-oxy)-2-p-chlorophenylacetic acid;
2-(1-ethyl-2-methyl-3-carboxyindolyl-5-oxy)-2-p-chlorophenylacetic acid;
2-(1-n-propyl-2-methyl-3-carboxyindolyl-5-oxy)-2-p-chlorophenylacetic acid;
2-(1-isopropyl-2-methyl-3-carboxyindolyl-5-oxy)-2-p-chlorophenylacetic acid;
2-(1-isobutyl-2-methyl-3-carboxyindolyl-5-oxy)-2-p-chlorophenylacetic acid;
2-(2-methyl-3-carboxyindolyl-5-oxy)-2-p-chlorophenylpropionic acid;
2-(1,2-dimethyl-3-carboxyindolyl-5-oxy)-2-p-chlorophenylpropionic acid;
2-(1-ethyl-2-methyl-3-carboxyindolyl-5-oxy)-2-p-chlorophenylpropionic acid;
2-(1-n-propyl-2-methyl-3-carboxyindolyl-5-oxy)-2-p-chlorophenylpropionic acid;
2-(1-isopropyl-2-methyl-3-carboxyindolyl-5-oxy)-2-p-chlorophenylpropionic acid, and
2-(1-isobutyl-2-methyl-3-carboxyindolyl-5-oxy)-2-p-chlorophenylpropionic acid.

d. A mixture of 0.78 g. of NaNH$_2$ and 3.67 g. of 2-(1,2-dimethyl-3-carbethoxyindolyl-5-oxy)-2-phenylacetic acid in 30 ml. of THF is warmed slowly to 70° with stirring. The mixture is cooled to 20° and 20 ml. of HMPT are added. The mixture is cooled to 0° and 1.5 g. of methyl iodide are added dropwise at 0°. The mixture is then heated and stirred at 70° for 3 hours and is evaporated. After customary work-up, 2-(1,2-dimethyl-3-carbethoxyindolyl-5-oxy)-2-phenylpropionic acid is obtained.

e. 3.33 g. of 2-(2-methyl-3-carbethoxyindolyl-5-oxy)-2-methylpropionic acid ethyl ester are dissolved in 25 ml. of DMF and 0.24 g. of NaH is added with stirring and cooling. The mixture is stirred for 30 minutes more and a solution of 2 g. of isobutyl bromide in 10 ml. of DMF is added. The mixture is stirred overnight at 25°, mixed with water and methylene chloride and worked up. After chromatography of the residue on silica gel, ester Ih is obtained.

EXAMPLE 2

2.75 g. of 1-isobutyl-2-methyl-3-carbethoxy-5-hydroxyindole are added to a suspension of 0.24 g. of NaH in 20 ml. of dimethylacetamide. The mixture is stirred for 1 hour at 20° and 1.95 g. of 2-bromo-2-methylpropionic acid ethyl ester are added. The mixture is maintained at 90° for 20 hours after which it is cooled, mixed with water and extracted with ether. The ether solution is washed twice with dilute sodium hydroxide solution and is evaporated after drying. Ester Ih is obtained.

EXAMPLE 3

A mixture of 2.75 g. of 1-isobutyl-2-methyl-3-carbethoxy-5-hydroxyindole and 0.23 g. of sodium in 50 ml. of xylene is heated under reflux for 3 hours. It is then allowed to cool to 20°. 1.95 g. of 2-bromo-2-methylpropionic acid ethyl ester in 10 ml. of xylene are added and the resulting suspension is stirred for 6 hours under reflux and cooled. 2 ml. of ethanol are added. The inorganic precipitate is filtered off. The filtrate is evaporated and the residue taken up in ether. The solution is washed with NaHCO$_3$ solution and saturated NaCl solution, dried over MgSO$_4$ and evaporated. Ester Ih is obtained.

EXAMPLE 4

1.5 g. of sulfuric acid are added to a mixture of 2.75 g. of 1-isobutyl-2-methyl-3-carbethoxy-5-hydroxyindole and 1.32 g. of 2-hydroxy-2-methylpropionic acid ethyl ester and the reaction mixture is stirred for 2 hours at 50°-60°. After cooling, the reaction mixture is mixed with water and brought to pH 8 with dilute sodium hydroxide solution. The aqueous phase is extracted with ether. The ether extract is dried and evaporated; ester Ih is obtained.

EXAMPLE 5 a. 2.75 g. of 1-isobutyl-2-methyl-3-carbethoxy-5-hydroxyindole are dissolved in 20 ml. of acetone to which 0.4 g. of NaOH are added with stirring, and then 1.67 g. of 2-bromo-2-methylpropionic acid in 6 ml. of acetone are added dropwise with stirring and heating under reflux. The mixture is stirred for an hour more at 56° and then left for 24 hours. Acetone is distilled off and the residue is dissolved in 100 ml. of water. The solution is repeatedly washed with ether and acidified to pH 4 with HCl. Acid Ii is obtained.

b. 1 g. of Ii is dissolved in 20 ml. of ether and a solution of diazomethane in ether is added dropwise until the yellow coloration persists. After evaporation, 2-(1-isobutyl-2-methyl-3-carbethoxyindolyl-5-oxy)-2-methylpropionic acid methyl ester is obtained.

c. 1 g. of acid Ii (or 1g. of 2-(1-isobutyl-2-methyl-3-carboxyindolyl-5-oxy)-2-methylpropionic acid) is dissolved in 40 ml. of a saturated solution of hydrochloric acid in ethanol and the mixture is allowed to stand for 12 hours at 20°, heated under reflux for 2 hours and evaporated. The residue is dissolved in water and the aqueous solution adjusted to pH 8 with dilute sodium hydroxide solution and extracted with ethyl acetate. The extract is dried and evaporated; ester Ih is obtained.

EXAMPLE 6

1 g. of 2-(1-isobutyl-2-methyl-3-carbethoxyindolyl-5-oxy)-2-methylpropionitrile, obtainable from 1-isobutyl-2-methyl-3-carbethoxy-5-hydroxyindole and 2-bromo-2-methylpropionitrile, is heated under reflux with 1 g. of KOH in 10 ml. of ethanol and 1 ml. of water for 40 hours. The mixture is evaporated and water is added to the residue. The solution is extracted with ether and brought to pH 5 with hydrochloric acid. 2-(1-Isobutyl-2-methyl-3-carboxyindolyl-5-oxy)-2-methylpropionic acid is obtained.

EXAMPLE 7

1 g. of 2-(1-isobutyl-2-methyl-3-carbethoxyindolyl-5-oxy)-2-methylpropionitrile is heated under reflux with 6 ml. of acetic acid and 6 ml. of concentrated hydrochloric acid for 2 hours under nitrogen. The mixture is evaporated and the residue is dissolved in dilute NaOH. The resulting solution is extracted with ether and brought to pH 5 with hydrochloric acid. Acid Ii is obtained.

EXAMPLE 8

3 g. of 2-(1-isobutyl-2-methyl-3-carbethoxyindolyl-5-oxy)-2-methylpropionamide, obtainable from 1-isobutyl-2-methyl-3-carbethoxy-5-hydroxyindole and 2-bromo-2-methylpropionamide, and 5 g. of KOH in 100 ml. of ethanol are heated under reflux under nitrogen for 3 hours. The mixture is evaporated and water is added to the residue. The solution is extracted with ether and brought to pH 5 with hydrochloric acid. Acid Ii is obtained.

The examples which follow relate to pharmaceutical preparations containing active compounds of Formula I or physiologically acceptable salts thereof:

EXAMPLE A: Tablets

A mixture of 1 kg. of acid Ii, 4 kg. of lactose, 1.2 kg. of potato starch, 0.2 kg. of talc and 0.1 kg. of magnesium stearate is pressed in the usual manner to form tablets, each of which contains 100 mg. of active compound.

EXAMPLE B: Dragees

Tablets are pressed in accordance with Example A and coated in the usual manner with a coating consisting of sugar, maize starch, talc, tragacanth and dyestuff.

EXAMPLE C: Capsules 5 kg. of acid Ii are packed into hard gelatin capsules in the usual manner, so that each capsule contains 250 mg. of active compound.

Tablets, dragees and capsules containing one or more of the other active compounds of Formula I and/or physiologically acceptable salts thereof can be obtained analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An indole compound of the formula

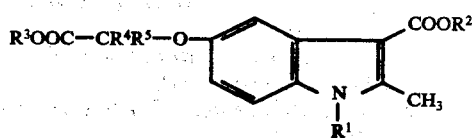

wherein $R^1$, $R^2$ and $R^3$ are identical or different and each is H or alkyl of 1–6 carbon atoms; $R^4$ is H or methyl and $R^5$ is, phenyl or chlorophenyl, and physiologically acceptable salts thereof.

2. A compound of claim 1, wherein $R^1$ is H or alkyl of 1–4 carbon atoms.

3. A compound of claim 1, wherein $R^1$ is H, methyl, ethyl, n-propyl, isopropyl or isobutyl.

4. A compound of claim 1, wherein $R^2$ is H, methyl or ethyl.

5. A compound of claim 1, wherein $R^2$ is H.

6. A compound of claim 1, wherein $R^2$ is methyl or ethyl.

7. A compound of claim 1, wherein $R^3$ is H, methyl or ethyl.

8. A compound of claim 1, wherein $R^3$ is H.

9. A compound of claim 1, wherein $R^3$ is methyl or ethyl.

10. 2-(1-Isobutyl-2-methyl-3-carbethoxyindolyl-5-oxy)-2-phenylpropionic acid, a compound of claim 1.

11. 2-(1-Isobutyl-2-methyl-3-carbethoxyindolyl-5-oxy)-2-phenylpropionic acid ethyl ester, a compound of claim 1.

12. A cholesterol-lowering pharmaceutical preparation comprising a compound of claim 1, in admixture with a pharmaceutically-acceptable carrier.

13. A method of lowering the cholesterol level in the blood of mammals comprising administering to a patient a daily dosage of a compound of claim 1, in admixture with a pharmaceutically-acceptable carrier, effective to lower the cholesterol level.

14. The method of claim 13, wherein the daily dosage is 0.2–20 mg./kg. of body weight.

15. The method of claim 13, wherein the compound is 2-(1-isobutyl-2-methyl-3-carbethoxyindolyl-5-oxy)-2-phenylpropionic acid.